United States Patent [19]

Mueller-Kirschbaum et al.

[11] Patent Number: 5,404,606
[45] Date of Patent: Apr. 11, 1995

[54] PROCESS AND DEVICE FOR WASHING

[75] Inventors: Thomas Mueller-Kirschbaum, Solingen; Eduard Smulders, Hilden; Wolfgang Hoefer, Duesseldorf, all of Germany

[73] Assignee: Henkel Kommanditgesellscaft auf Aktien, Duesseldorf, Germany

[21] Appl. No.: 133,207
[22] PCT Filed: Apr. 7, 1992
[86] PCT No.: PCT/EP92/00785
§ 371 Date: Dec. 13, 1993
§ 102(e) Date: Dec. 13, 1993
[87] PCT Pub. No.: WO92/18680
PCT Pub. Date: Oct. 29, 1992

[30] Foreign Application Priority Data

Apr. 16, 1991 [DE] Germany ............... 41 12 417.0

[51] Int. Cl.⁶ ............... D06F 33/02; D06F 39/02
[52] U.S. Cl. ....................... 8/158; 68/12.02; 68/12.18; 68/17 R
[58] Field of Search ............. 8/158; 68/12.02, 12.18, 68/17 R

[56] References Cited

U.S. PATENT DOCUMENTS

| | | | |
|---|---|---|---|
| 3,645,669 | 2/1972 | Rausch | 8/137 |
| 3,881,344 | 5/1975 | Jobe | 73/64.4 |
| 4,416,148 | 11/1983 | Klus et al. | 73/64.4 |

FOREIGN PATENT DOCUMENTS

| | | | |
|---|---|---|---|
| 41070 | 4/1978 | Japan | 68/12.02 |
| 210296 | 10/1985 | Japan | 68/12.18 |
| 2217050 | 10/1989 | United Kingdom | 68/17 R |

OTHER PUBLICATIONS

JAOCS, vol. 63, No. 7 (Jul. 1986) pp. 932 to 934.
Journal of Applied Polymer Science, vol. 28, 1983, "On-Line Measurement of Surface Tension and Density with Applications to Emulsion Polymerization", F. J. Schork and W. H. Ray, pp. 407 to 430.
Laboratory Practice, Dec. 1984, "A versatile pressure transducer" Rosenthal and Thorne.

Primary Examiner—Philip R. Coe
Attorney, Agent, or Firm—Ernest G. Szoke; Wayne C. Jaeschke; Norvell E. Wisdom

[57] ABSTRACT

The invention concerns a process for washing fibrous materials, skins, textile materials or the like using an aqueous, surfactant containing washing liquid obtained by adding washing agents to water. The minimal dispensed amounts as determined in subsequent washing tests are always obtained automatically, without the cleaning power and the cleaning efficiency being reduced to unacceptable levels. To this end, the surface tension of the washing liquid is measured during the washing process using a tensiometer. The actual washing agent concentration is derived from these measured values and an initial concentration is derived from the quantity of washing agent added. The detergency is calculated from this initial concentration. The addition of a washing agent is discontinued when no further increase occurs in the detergency. The invention also concerns a device for carrying out the process. The device has capillaries connected to constant gas flow sources and immersed to the same depth in the washing liquid. The capillaries are connected to a device for determining the pressure or the frequency of pressure variations which controls a dispensing unit via an evaluation unit.

20 Claims, 7 Drawing Sheets

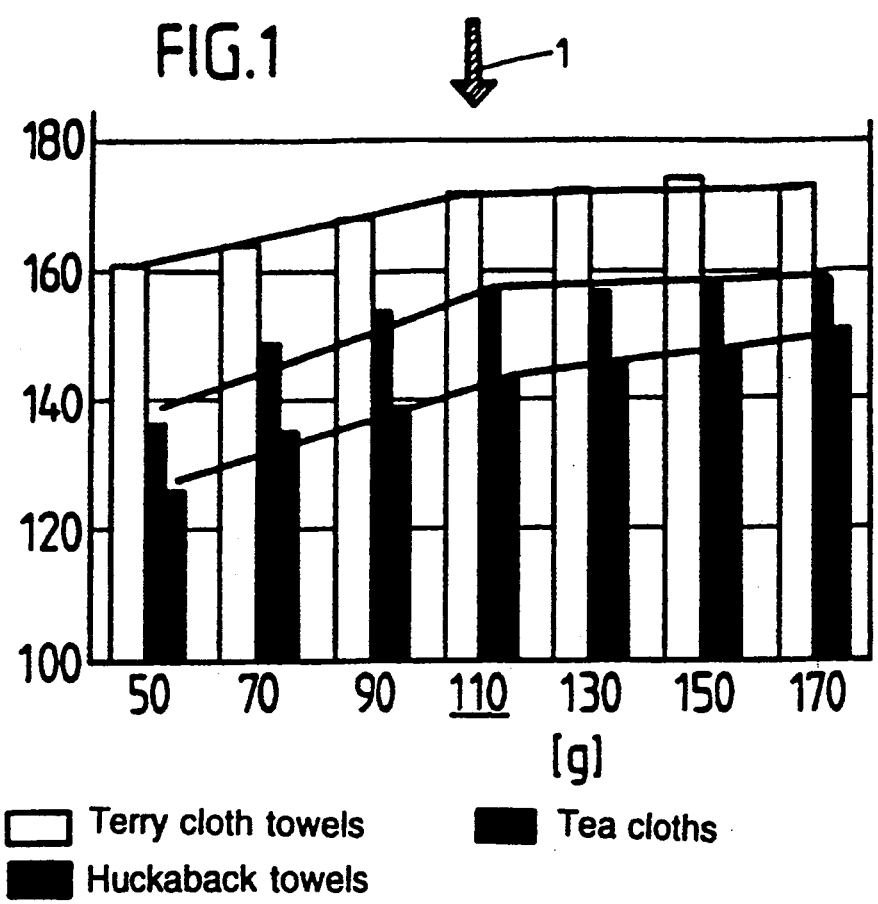
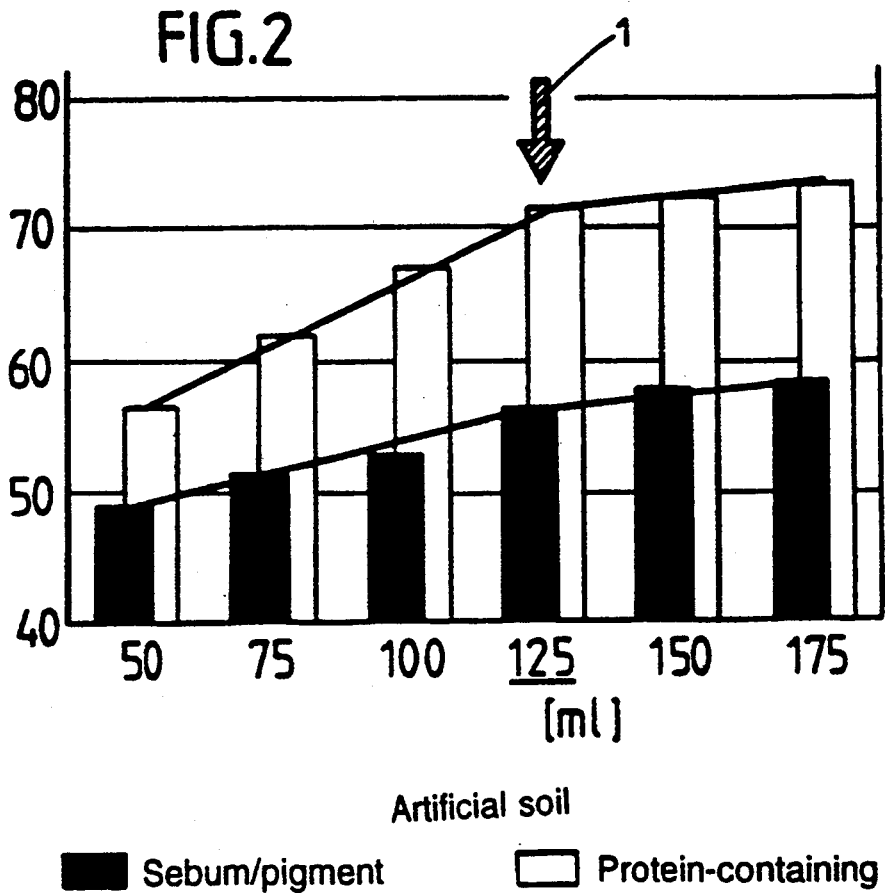

PROCESS AND DEVICE FOR WASHING

FIELD OF THE INVENTION

This invention relates to a process for washing fibrous materials, skins, textile materials or the like with a water-based surfactant-containing washing liquid which is obtained by addition of detergents to water.

STATEMENT OF RELATED ART

For some time, the washing processes carried out in the institutional sector and in the home have been the target of efforts to achieve ecological and economic improvements in the processes. These efforts have been aimed at reducing the consumption of energy, detergent, water and time. To achieve these objectives, special dispensing systems and dispensing processes are often used. A particular difficulty involved in the use of special dispensing processes is that, on the one hand, as little detergent and water and possible should be used although, on the other hand, the amounts dispensed should not fall below the minimum levels dependent on a number of parameters to ensure that detergency and washing performance do not to fall to unacceptable levels. There is an optimal detergent concentration for every type of material to be washed, soils, water hardnesses and detergents and also temperatures and the type of mechanical agitation. This concentration can be determined purely empirically from the fact that, if the concentration falls below this optimum, the washing result falls to unacceptable levels and, if the optimum is exceeded, no improvement is obtained in the washing result. In order always to achieve the optimal dispensing of detergent in practice under highly variable conditions, the optimal washing point mentioned has to be automatically determined during the washing process itself.

It is known from JAOCS, Vol. 1963, 1986, pages 931 to 943, that the surface tension of the washing water used in a mechanical washing machine can be measured and the result of the measurement subsequently used to control the addition of detergents. However, it is not known whether and in what way the optimal washing point can be determined in a process for washing fibrous materials, skins, textile materials or the like by the measurement of surface tension and then used to control the addition of detergents. In other known washing processes, dispensing of the detergent is controlled by measurement of the conductivity, the pH value and the degree of clouding (*Laboratory Practice*, 1984, page 69). Unfortunately, these known dispensing processes give unsatisfactory results. U.S. Pat. Nos. 3,881,344 and 4,416,148 are cited as further relevant prior art.

DESCRIPTION OF THE INVENTION

Object of the Invention

Accordingly, the problem addressed by the present invention was always to achieve the minimum dispensed amounts determinable in subsequent washing tests automatically without a reduction in detergency and washing performance to unacceptable levels. In addition, this problem was to be solved irrespective of the washing conditions, such as the type of materials to be washed, the detergent, the water hardness, the mechanics, the soils, etc., without the process according to the invention having to be specially adapted to these washing conditions.

SUMMARY OF THE INVENTION

According to the invention, the solution to this problem is characterized in that the surface tension of the washing liquid is measured, more particularly continuously, with a tensiometer during the washing process; that the actual detergent concentration (Value 1) is ascertained from these measured values; that from the quantity of detergent added, a concentration with respect to detergent (Value 2) is ascertained, more particularly continuously; that the Detergent Effect (Value 1 - Value 2)/Value 2 is calculated; and that the addition of detergent is terminated when there is no further increase in the Detergent Effect. A bubble tensiometer operated with sufficiently constant gas streams, particularly air streams, is advantageously used for this purpose.

It is important in this regard that only the change as a function of time and not the absolute value of the Detergent Effect goes into the control of the amount of detergent dispensed. Because the maximum detergent effect is dependent upon the degree of soiling, the detergent and other washing conditions, the process can thus be universally used, without having to be specially adapted to certain washing conditions. The bubble tensiometer mentioned is known per se and is described, for example, by F. J. Schork and W. H. Rey in *Journal of Applied Polymer Science*, Vol. 28, 1983, pages 407 to 430, so that there is no need for any further description in the present specification.

The optimal washing point mentioned above is reached automatically in the process according to the invention because, as shown hereinafter, this point coincides with the maximum of the magnitude of the Detergent Effect, i.e. with its optimum.

DESCRIPTION OF PREFERRED EMBODIMENTS

In one advantageous embodiment in which the Detergent Effect can be determined very accurately, the detergent is added discontinuously in several individual portions and the Detergent Effect is determined from a point in time when there is no further significant increase in surface tension after the addition of one of the portions.

A further saving of time and energy is achieved if the wash cycle is terminated during or after termination of addition of the detergent. Pumping off and/or rinsing can then be commenced.

In the determination of surface tension, it is possible on the one hand to measure the difference between the maximum bubble pressures and, on the other hand, to determine the rate at which the bubbles flow from the bubble tensiometer as a function of time. The first of these two methods is preferred.

It is also important that the tensiometer is operated with constant gas streams. These can be produced by regulation of variable gas streams or even by uniformly operating pumps.

The process according to the invention is suitable for dispensing both liquid and solid or paste-form detergents.

According to the invention, various possibilities are available for regulating the amount of detergent dispensed. In one simple version, the washing liquid may be agitated and the surface tension measured in an alternating sequence. Depending on the result of the measurement, more detergent is added or the addition of detergent is stopped. On the other hand, in a washing process where the washing liquid is continuously circulated, the surface tension of the circulating part of the washing liquid can be measured, more particularly continuously. The only requirement governing the measurement of surface tension is that the liquid should not be agitated too vigorously in the vicinity of the tensiometer. On the other hand, however, a major advantage of the process according to the invention lies in the extremely small volume of washing liquid required for the tensiometer so that, by simple modification, the process according to the invention as claimed in the first claim can be carried out in a number of different types of washing machines without having to change the programs or controls or the washing effect properties of the washing machines. Thus, on the other hand, surface tension can also be measured in the liquor pumped off.

In another embodiment of the invention, the dependence of surface tension on temperature is corrected during the measurement. This can be done by incorporation of the values measured by a thermosensor in the regulation of the amount dispensed.

According to the invention, not only can the necessary quantity of detergent and hence the necessary washing time be reduced, which also minimizes energy, the quantity of rinsing water required for the washing process can also be reduced. This is because, in another embodiment, rinsing is terminated when the measured surface tension exceeds a predetermined maximum value.

The invention relates not only to the washing process described in the foregoing, but also to apparatus for carrying out the process. In this apparatus, the solution to the problem addressed by the invention is characterized in that capillaries connected to constant gas stream sources and dipping to equal depths into the washing liquid are provided and are connected to means for measuring the pressure or the frequency of changes in pressure which control a dispensing unit for the detergent via an evaluation unit.

To reduce the quantity of rinsing water, the evaluation unit of the apparatus according to the invention is connected to a control element which actuates rinsing.

BRIEF DESCRIPTION OF THE DRAWINGS

Embodiments of the invention are described in detail in the following with reference to the accompanying drawings, wherein:

FIG. 1 shows washing results determined by a standard process for powder-form universal detergent plotted against the amount dispensed.

FIG. 2 shows washing results for liquid universal detergents likewise determined by a standard method plotted against the amount dispensed.

EXAMPLES

The washing tests described in the following were carried out with a powder-form universal detergent and with a liquid universal detergent. The laundry to be washed consisted of 3.5 kg of normally soiled domestic washing with and without additional standard soils. A one-wash cycle was used with an amount of 50 to 170 g of the powder-form detergent divided into portions of 20 g and 50 to 175 ml of the liquid detergent divided into portions of 25 ml. The washing temperature was 60° C. To evaluate the washing tests, samples of 1 liter of wash liquor were removed during the first pumping-off phase.

To ascertain the optimal amount of detergents, washing tests are usually carried out with different amounts and different items of laundry and the reflectance spectra of the laundry items is subsequently measured. FIGS. 1 and 2 show results such as these obtained in known manner. FIG. 1 shows the Berger whiteness values for terry towels, tea cloths and huckaback towels after 15 washes with a powder-form universal detergent in a one-wash cycle at 60° C. It can be seen from this graph that the whiteness values increase with increasing dosage until a plateau is reached with an amount of around 110 g. This amount represents the optimal washing point marked with an arrow 1. Accordingly, these measurements can only be carried out on completion of the washing process.

FIG. 2 shows a corresponding graph for a liquid universal detergent. In this case, reflectance is plotted in percent against the amount of detergent. The washing results were again obtained in a one-wash cycle at 60° C. As in FIG. 1, the washing result, the single wash cycle performance, increases until it reaches a plateau at an amount of 125 ml. In this case, therefore, this amount forms the optimal washing point marked by the arrow 1.

Figure 3:
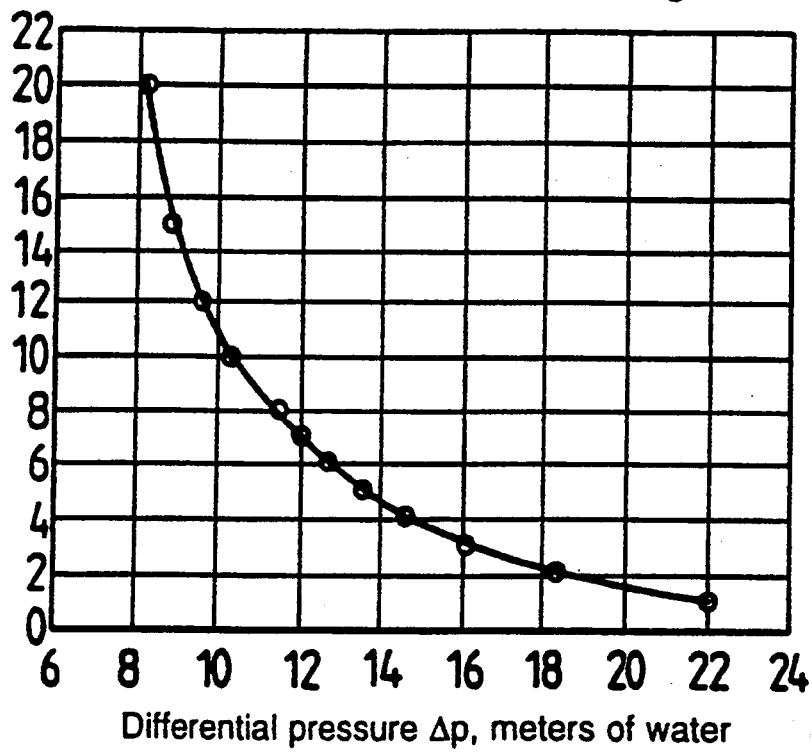
FIG. 3 shows the relationship between the concentration of a powder-form universal detergent and the measured pressure difference of the tensiometer.
Figure 4:
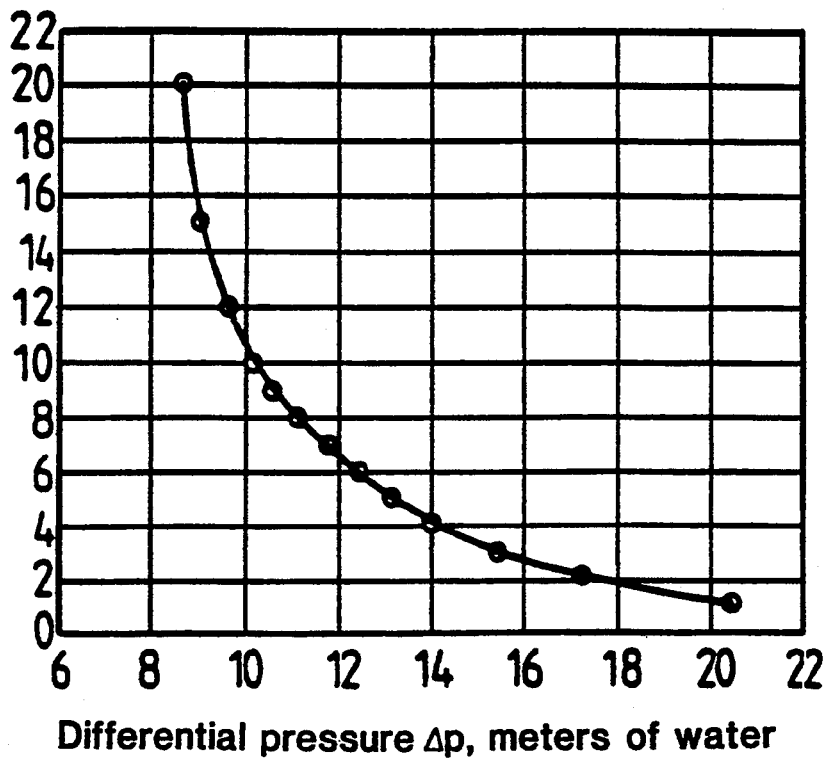
FIG. 4 shows the same for a liquid universal detergent.

It is shown hereinafter how, in accordance with the invention, this optimal washing point can actually be determined during the washing process and used for automatically controlling the dispensing of a washing machine. To this end, the concentration of detergent in the wash liquor has to be determined from the values obtained with a tensiometer. As shown in FIGS. 3 and 4, there is a clear and unambiguous relationship between this concentration and the pressure difference as measured with the tensiometer. A corresponding relationship exists between the concentration and the pressure variation rate as measured with the tensiometer, so that it could also be used as an alternative in the process according to the invention. Accordingly, FIG. 3 shows a calibration curve for a powder-form universal detergent while FIG. 4 shows a corresponding curve for a liquid universal detergent.

Figure 5:
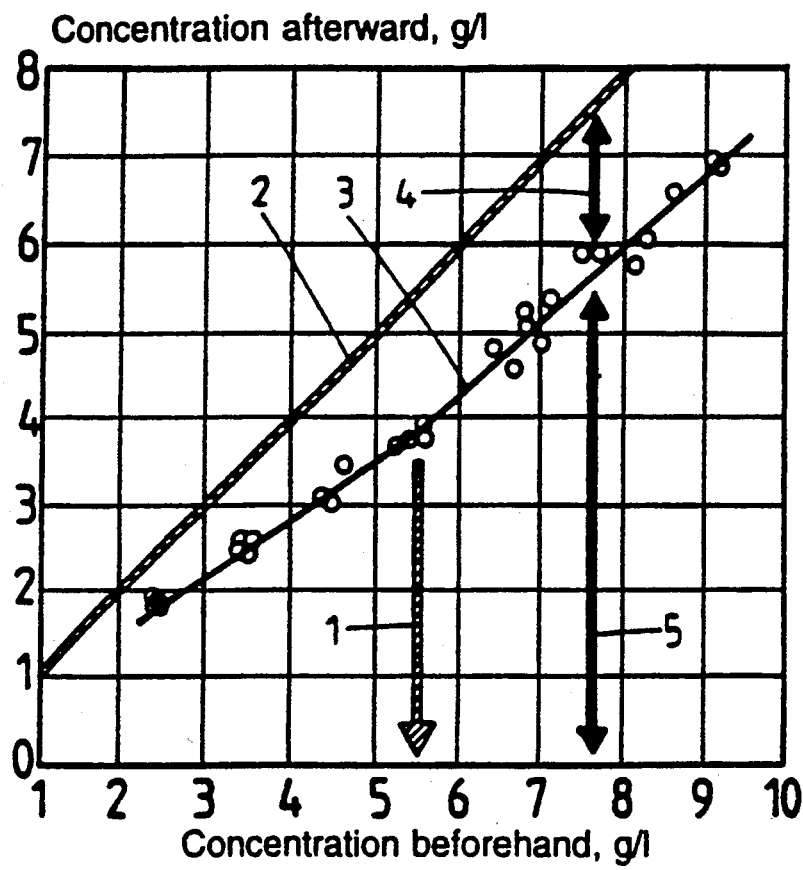
FIG. 5 shows the changes in concentration of a wash liquor in consequence of the washing process as a function of the concentration for a powder-form universal detergent.
Figure 6:
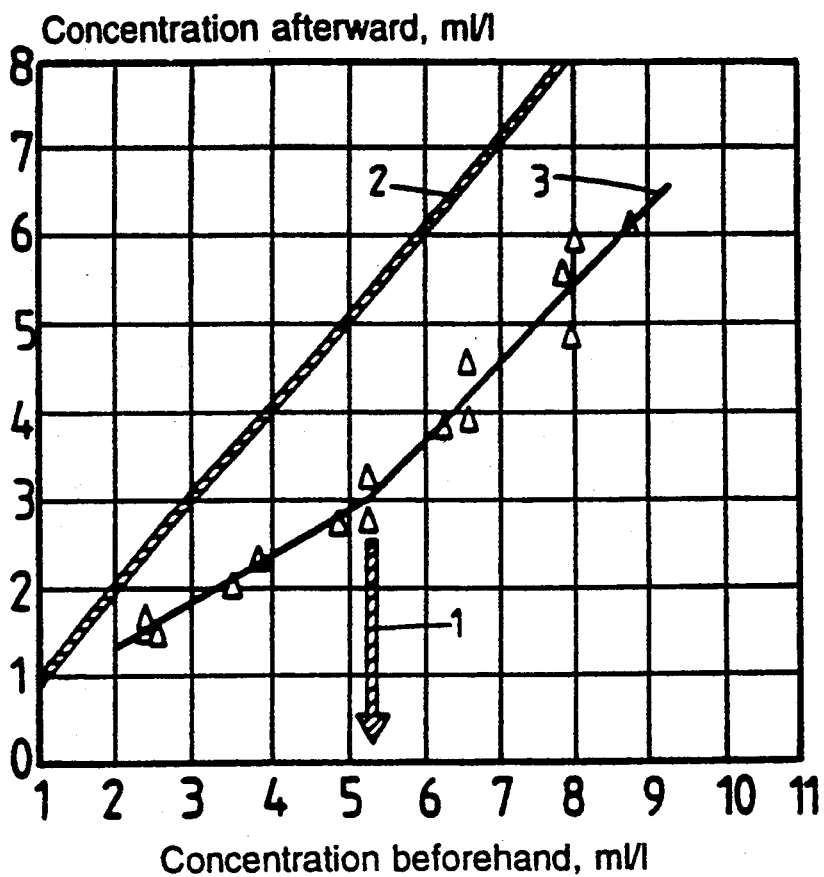
FIG. 6 shows the same for a liquid universal detergent and laundry without standard soils.
Figure 7:
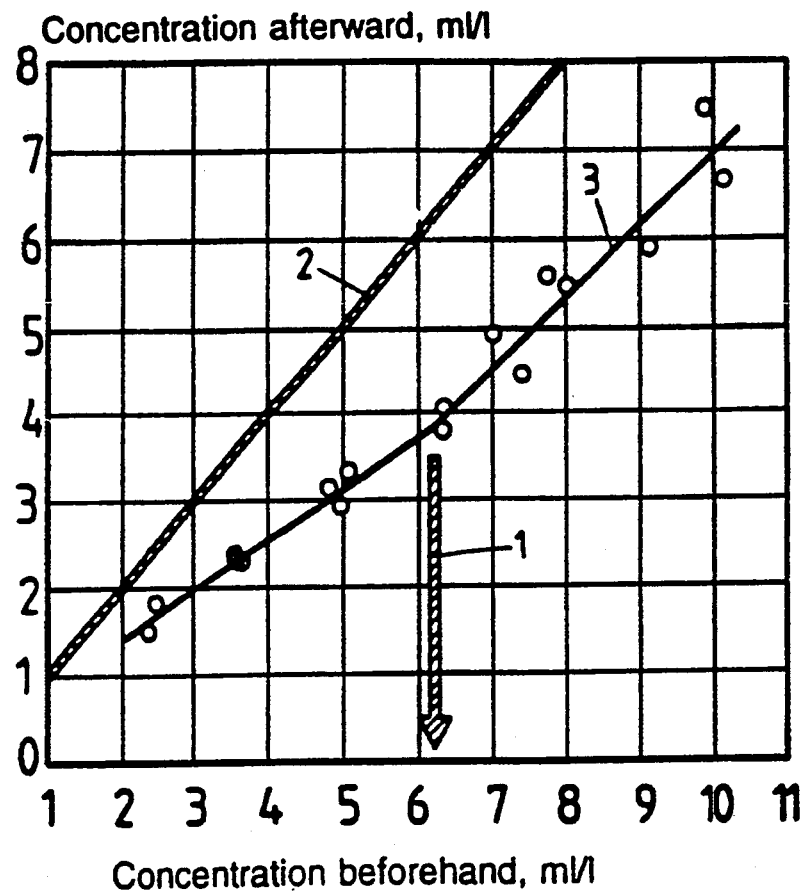
FIG. 7 shows the same for a liquid universal detergent and laundry with standard soils.

The graphs in FIGS. 5, 6 and 7 explain the principle on which the optimal washing point can be determined with a tensiometer in accordance with the present invention. In FIG. 5, the concentration values of wash liquors obtained from tensiometer measurements, which were referred to earlier as Value 1, are plotted against the concentration calculated from the quantity of detergent added and the quantity of water. These values were measured for wash liquors obtained after the washing of 3.5 kg of normally soiled domestic washing with a powder-form universal detergent. The concentration values calculated from the quantity of detergent added and the quantity of water correspond to the concentration values with respect to the wash liquor before the washing process and were referred to earlier on as Value 2.

Without the influence of the soiled domestic washing, the line 2 of equal concentration would be obtained. In fact, however, the line 3 is obtained after the washing process. The difference between the two lines 2 and 3 marked by the double arrow 4 represents the quantity of detergent which was adsorbed onto soil and fabrics. By contrast, the double arrow 5 marks the quantity of detergent remaining behind in the liquor after washing. It can be seen from FIG. 5 that line 3 curves upwards at a concentration of 5.5 g/l. This effect can be explained by the fact that, with relatively high concentrations, no further detergent is adsorbed onto soil and fabrics and any detergent additionally introduced passes straight into the wash liquor. The concentration of 5.5 g/l corresponds to an addition of 110 g for 3.5 kg of normally soiled domestic washing and hence to the optimal washing point, as shown in FIG. 1. Accordingly, this optimal dosage is again marked by the arrow 1. Both here and in the other Figures, the same items are denoted by the same reference numerals.

FIG. 6 shows the same relationship as FIG. 5, but for liquid universal detergents and normally soiled domestic washing without standard soils. In this case, the bend in line 3 occurs at a Value 2 of 5.2 ml/l which corresponds to an addition of 104 ml for 3.5 kg of normally soiled domestic washing. The value also corresponds fairly closely to the optimal washing point determined by standard methods as shown in FIGS. 1 and 2.

FIG. 7 shows the same relationship as FIG. 6, but for normally soiled domestic washing with additional standard soils. In this case, the bend in line 3 occurs at a Value 2 of 6.1 ml/l, which corresponds to an addition of 122 ml for 3.5 kg of normally soiled domestic washing. A comparison with FIG. 2 shows that in this case, too, the bend in curve 3 occurs at the optimal washing point.

In order to utilize the relationships just described to develop an automatic dispensing or metering system, the variable "Detergent Effect" (DE) is defined as the quotient from the difference in concentration before and after washing, which is marked in FIG. 5 by the double arrow 4, and the concentration before washing. Accordingly, the variable in question is (Value 2 - Value 1)/Value 2. As will be shown, the optimal washing point is situated at that quantity of detergent for which the Detergent Effect DE reaches its maximum. At this washing point, as much detergent as necessary is used for adsorbing soil, although at the same time as little detergent as possible passes unused into the wastewater.

Accordingly, the following information can be derived from the results illustrated in FIGS. 5 to 7. The quantity of detergent used to adsorb soil increases with increasing input of detergent, as does the quantity of detergent remaining in the liquor after washing. Beyond a certain limiting concentration, however, the quantity of detergent remaining in the liquor increases to a greater extent than the quantity required to adsorb soil. Accordingly, there is an optimal ratio between the quantity of detergent used for dispersing or emulsifying soil and the quantity of detergent remaining behind in the wash liquor which does not contribute towards soil adsorption.

Figure 8:
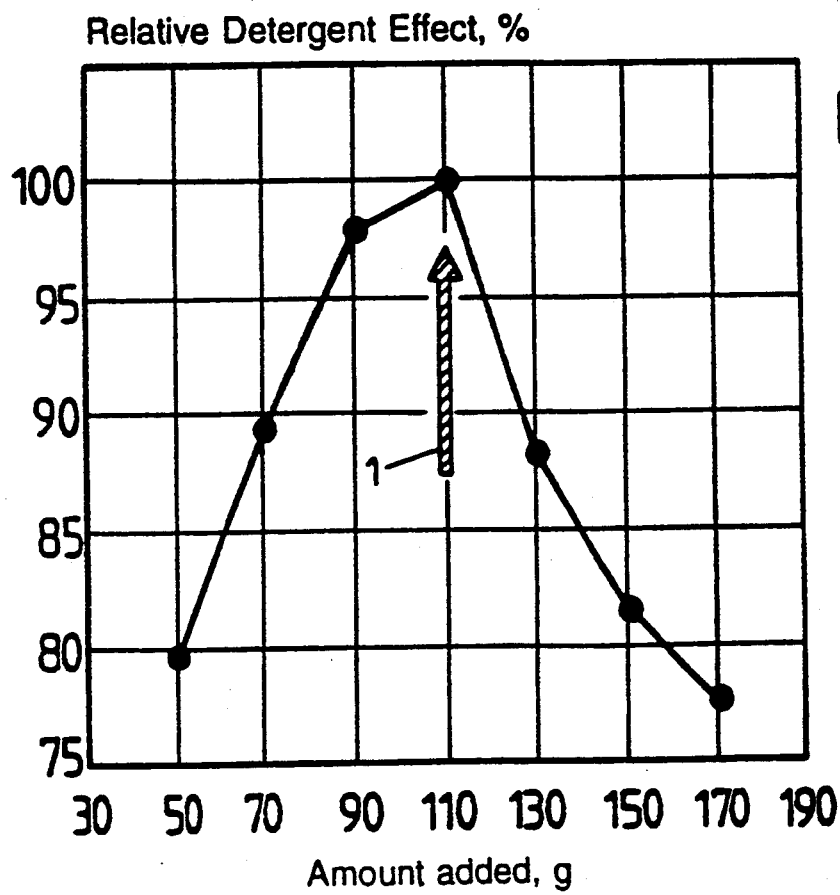
FIG. 8 shows the relative Detergent Effect as determined from tensiometer measurements for a powder-form universal detergent.
Figure 9:
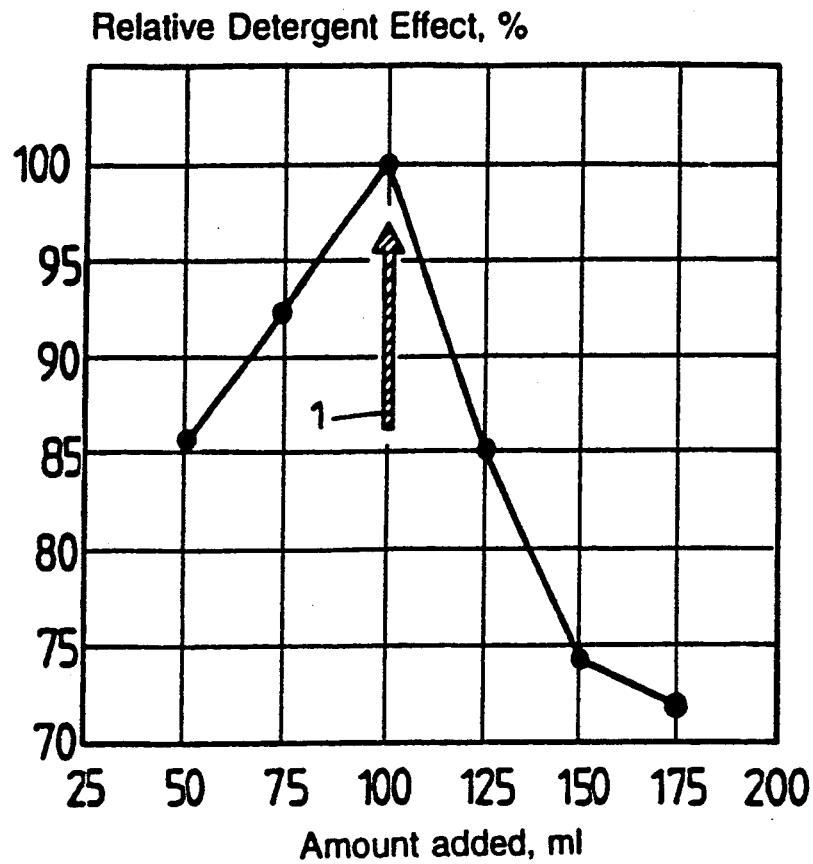
FIG. 9 shows the same for a liquid universal detergent and laundry without standard soils.
Figure 10:
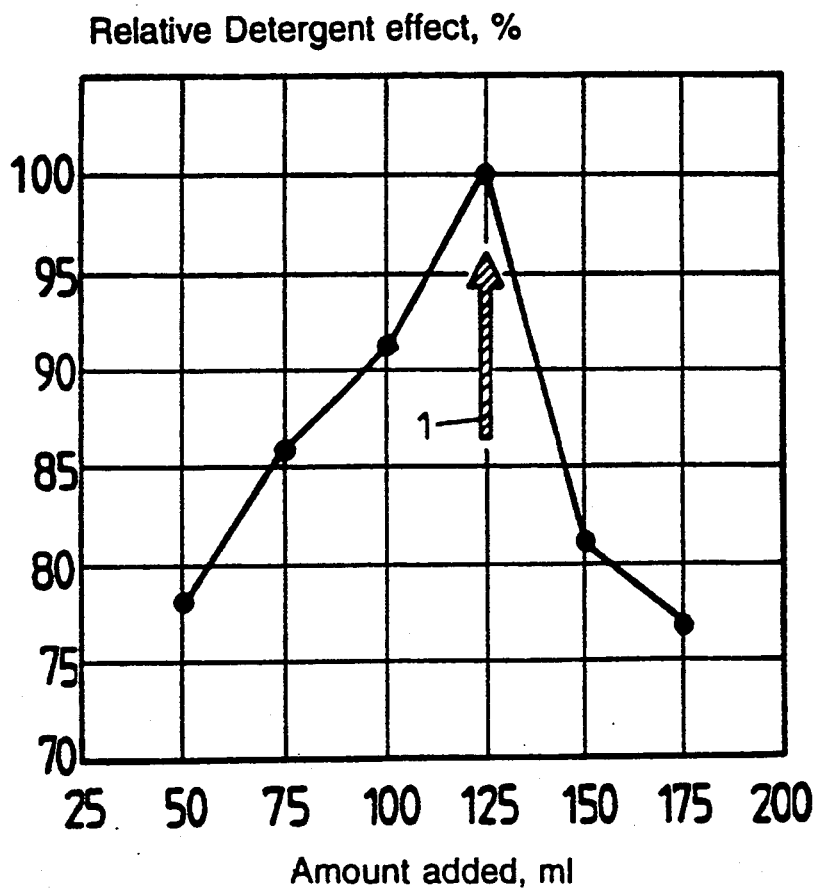
FIG. 10 shows the same for laundry with standard soils.

In FIGS. 8 to 10, the Detergent Effect is illustrated as a function of the dosage under certain conditions. In this case, the "Relative Detergent Effect" is recorded as the quotient from the Detergent Effect and the maximum Detergent Effect under the particular washing conditions prevailing. The results in FIG. 8 were obtained with powder-form universal detergent while the results in FIGS. 9 and 10 were obtained with liquid universal detergent—in FIG. 9 for washing without standard soils and in FIG. 10 for washing with additional standard soils. Comparison of the maximal values of the Relative Detergent Effect with the optimal washing points determined in FIGS. 1 and 2 leads to the conclusion that the maximum of the Relative Detergent Effect coincides exactly with this optimal washing point. If, therefore, the particular relative or absolute Detergent Effects are determined from concentration measurements during the washing process in dependence upon the addition of detergent, the amount dispensed can be adjusted during the actual washing process in such a way that the optimal washing effect is achieved although the degree of soiling of the laundry and other parameters can differ from one wash to another.

Figure 11:
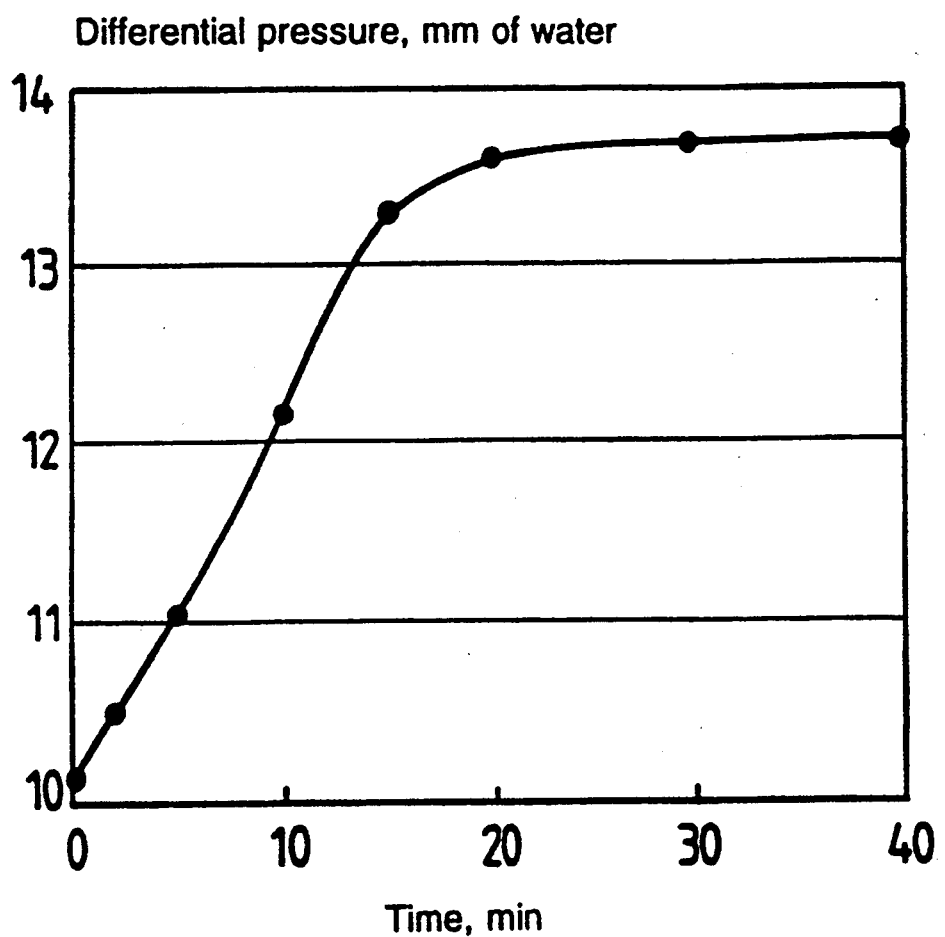
FIG. 11 shows the reduction in the washing reserve during a wash cycle plotted against time and measured with the tensiometer.

Thus, in one preferred embodiment of the process according to the invention, the detergent is added in portions, for example in portions of 10 g or 10 ml. After each addition, surface tension initially decreases, but then increases again during the dispersion of soil. When the surface tension has reached a substantially constant value, the Detergent Effect is determined from the quantity of detergent and water added up to that point and from the result of the tensiometer measurement now carried out. After another portion of the detergent has been added and the surface tension has fallen and risen again, the Detergent Effect is again determined when the surface tension reaches a substantially constant value which does not have to coincide with the previous constant value. If the value obtained for the Detergent Effect is lower than on the last occasion, the addition of detergent and the washing process arc terminated. If, however, the Detergent Effect increases, the cycle is repeated. In FIG. 11, the reduction in the washing reserve during the washing process, measured as the differential pressure of the tensiometer, is plotted against time. It can be seen how the surface tension increases during soil dispersion after the addition of a portion of detergent, reaching a substantially constant value after a certain time, as just explained.

Figure 12:
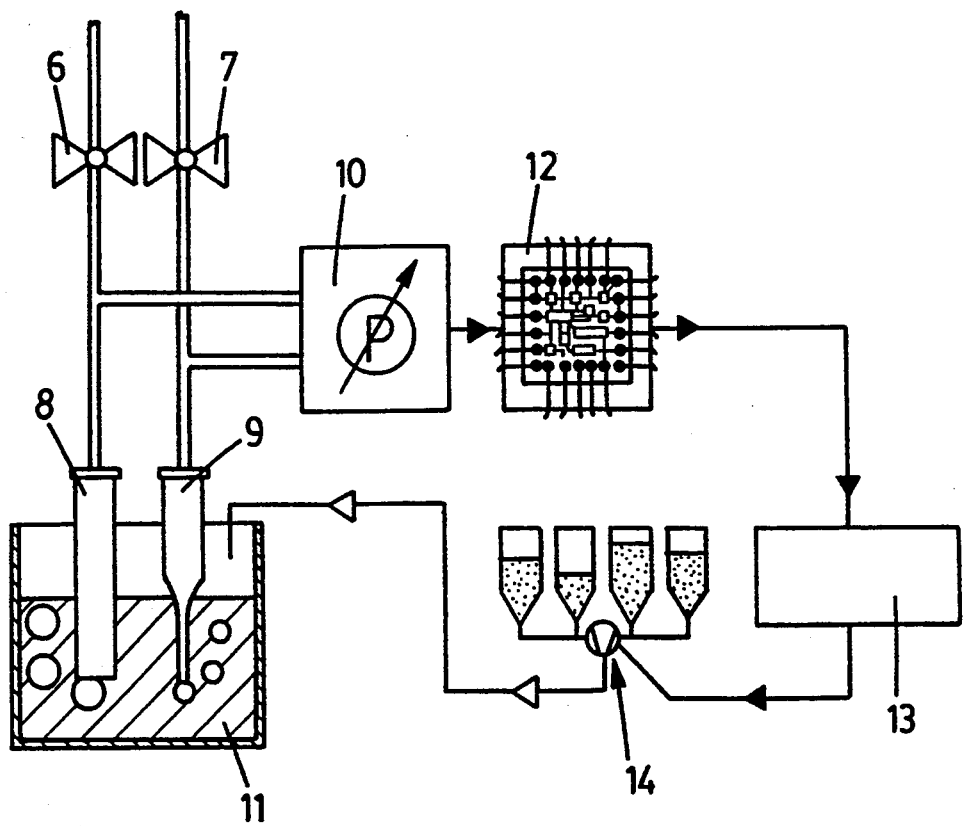
FIG. 12 schematically illustrates one embodiment of the apparatus according to the invention.

FIG. 12 shows one embodiment of apparatus according to the invention. In this case, the tensiometer was operated with compressed air. To achieve constant air streams, the compressed air is regulated by the valves 6 and 7 before being delivered to two capillaries 8 and 9. These capillaries dip into the wash liquor 11. The pressure difference between the feeds to the two capillaries 8 and 9 is determined by a measuring instrument 10. The measurements are evaluated by a computer 12 to obtain the surface tension, the concentration of surfactant and the Detergent Effect. These values are fed to a dispensing control unit 13 which is connected to a dispensing unit 14 for liquid or solid detergent.

The invention claimed is:

1. A process for washing fibrous materials, skins, or textile materials with a water-based surfactant-containing washing liquid comprising washing the materials by adding detergent to water, measuring the surface tension of the washing liquid with a tensiometer during the washing process, determining the actual detergent concentration (Value 1) and a concentration with respect to detergent (Value 2) from the surface tension measurements obtained and from the quantity of detergent added, respectively, calculating the Detergent Effect, defined as (Value 2 - Value 1)/Value 2, and terminating the addition of detergent when there is no further increase in the Detergent Effect.

2. A process as claimed in claim 1, wherein said tensiometer is a bubble tensiometer operated with constant gas streams.

3. A process as claimed in claim 2, wherein the detergent is added discontinuously in several individual portions and the Detergent Effect is calculated from a point in time when, after addition of one of the portions, there is no further significant increase in surface tension.

4. A process as claimed in claim 3, wherein the washing process is terminated during or after termination of the addition of detergent.

5. A process as claimed in claim 2 wherein to determine surface tension, the difference between the pressures of bubbles produced in the bubble tensiometer is measured.

6. A process as claimed in claim 2 wherein to determine surface tension, the rate at which bubbles flow from the bubble tensiometer is measured as a function of time.

7. A process as claimed in claim 2, wherein the constant gas streams are produced by regulation of variable gas streams or by uniformly operating pumps.

8. A process as claimed in claim 1 wherein the detergent is selected from the group consisting of a liquid, solid, paste-form detergent, and mixtures thereof.

9. A process as claimed in claim 1, wherein the washing liquid is agitated and surface tension is measured in an alternating sequence.

10. A process as claimed in claim 1 wherein the washing process is carried out with continuously circulating washing liquid and the surface tension of a circulating portion of the washing liquid is measured.

11. A process as claimed in claim 1 wherein the surface tension is measured in a washing liquid pumped off.

12. A process as claimed in claim 1 wherein the surface tension measurement is adjust to account for the dependence of surface tension on temperature.

13. A process as claimed in claim 1 further comprising performing a rinsing step after terminating the addition of detergent and terminating rinsing when the measured surface tension exceeds a predetermined maximal value.

14. Apparatus for controlling a process for washing fibrous materials, skins, or textile materials in a water-based surfactant-containing washing liquid obtained by repeated addition of detergent to water, said apparatus comprising means for washing, a bubble tensiometer which controls dispensing means for the detergent via evaluation means, wherein the bubble tensiometer comprises capillaries which are connected to constant gas stream sources and which dip into the washing liquid to equal depths, the capillaries being connected to means for determining the pressure difference or the frequency of changes in pressure between said gas stream sources, the evaluation means being capable of calculation of the actual detergent concentration (Value 1) from the measurements obtained, for calculation of the concentration with respect to detergent (Value 2) from the quantity of detergent and water added and for the calculation of the Detergent Effect (Value 2 - Value 1)/Value 2) and for actuation of the dispensing means so that it terminates the addition of detergent when there is no further increase in the Detergent Effect (Value 2 - Value 1)/Value 2).

15. Apparatus as claimed in claim 14 wherein the evaluation means is connected to a control element which actuates rinsing.

16. A process according to claim 1, wherein Value 1 and Value 2 are determined continuously.

17. A process according to claim 2, wherein the bubble tensiometer is operated with air streams.

18. A process as claimed in claim 1, wherein the detergent is added discontinuously in several individual portions and the Detergent Effect is calculated from a point in time when, after addition of one of the portions, there is no further significant increase in surface tension.

19. A process as claimed in claim 18, wherein the washing process is terminated during or after termination of the addition of detergent.

20. A process as claimed in claim 1, wherein the washing process is terminated during or after termination of the addition of detergent.

* * * * *